United States Patent [19]
Goto

[11] Patent Number: 5,800,369
[45] Date of Patent: Sep. 1, 1998

[54] LOAD REMOVING AND WALKING CAST FOR LOWER LEG

[75] Inventor: Takeshi Goto, Kurume, Japan

[73] Assignee: Castec Corporation, Kurume, Japan

[21] Appl. No.: 823,550

[22] Filed: Mar. 25, 1997

[51] Int. Cl.$^6$ .................................................. A61F 5/00
[52] U.S. Cl. .................................................. 602/6; 602/9
[58] Field of Search .......................... 602/3, 4, 5, 6–13

[56] References Cited

U.S. PATENT DOCUMENTS

| | | | |
|---|---|---|---|
| D. 135,026 | 2/1943 | Hirchfield | D23/384 |
| D. 172,321 | 5/1954 | Turner | D23/384 |
| 2,875,752 | 3/1959 | Lovich. | |
| 3,162,371 | 12/1964 | Palmer et al. | D23/384 |
| 4,565,250 | 1/1986 | Vasko. | |
| 4,888,225 | 12/1989 | Sandvig et al.. | |
| 5,002,047 | 3/1991 | Sandvig et al.. | |
| 5,015,002 | 5/1991 | Goodman et al. | D23/384 X |
| 5,520,621 | 5/1996 | Edenbaum et al.. | |
| 5,649,898 | 7/1997 | Goto | 602/6 |

FOREIGN PATENT DOCUMENTS

| | | |
|---|---|---|
| 5-5116 | 1/1993 | Japan. |
| 7-289582 | 11/1995 | Japan. |

OTHER PUBLICATIONS

The Journal of Bone and Joint Surgery, American Volume, Jul. 1967.

Primary Examiner—Richard J. Apley
Assistant Examiner—Kim M. Lee
Attorney, Agent, or Firm—Jacobson, Price, Holman & Stern, PLLC

[57] ABSTRACT

A cast having a predetermined space between a sole of a foot held in the cast and a bottom of the cast. The foot can be moved slightly so that a pushing-up action by the bottom of the cast toward the sole of the foot can be prevented, thereby providing a load removing effect. If the thickness of the space is changed, the load removing effect may be controlled.

7 Claims, 13 Drawing Sheets

( A1+ A2+A3)  ( P1+ P2+P3 )

LOAD REMOVING AND WALKING CAST FOR LOWER LEG

TECHNICAL FIELD OF THE INVENTION

The present invention relates to lower leg load removing and walking casts used for treatment of tibial fractures, that is, casts applied to an affected leg, and a method of making the same.

DESCRIPTION OF RELATED ART

PTB casts (Patellar Tendon Bearing casts, so-called walking casts for lower leg) as seen in FIG. 9 has broadly been employed to treat tibial fractures (fracture of leg bone). This cast is used for bearing a patient's human body weight at pressured parts around the knee joint (portions of the patellar tendon and tibial condyle) shown with arrows in FIG. 10 in order to enable a knee joint to move or walk with a working cast after having treated the leg bone or at an early period after a surgical operation, thereby protecting the tibial fractured portion so as not to effect an excessive load thereon.

However, there are still many unknown matters in regard to the effects of removal of load which is significant purpose of the cast, and accordingly not a few of the medical specialist feel dubious about the load removing effect. These specialists allow patient to rely on crutches for assisting the load removal over a long period of days even after having worn the cast for assisting the load removal.

In view of the above-mentioned circumstances, the inventor and associates used a dynamic foot pressure analysis system which was first introduced in Japan in 1992 and measured the load removing effect of the cast, and made studies on the actual load removing effects. Then, the load removing effect brought about by the prior cast was about only 30% of the patient's human body weight. This data tells us that 70% of the patient's weight is, when walking, burdened as a load on his fractured leg, and it was found that the load removing effect by the above-described broadly used cast was unsatisfied.

In an early healing period while the tibial fracture is not yet recovered, if the body weight is given upon a fractured limb, and the load removing effect is insufficient, the load force by the body weight is added as a disadvantageous pressure to the fractured part which results in causing curing difficulties such as a shortening deformity of the fractured part or delaying a healing of the fracture. However, the theoretical idea to allow the knee joint to move or to allow control of the walking as loaded at an early recovering time at which the cast aims, is very important for healing the tibial fracture. Therefore, if the cast decreases or enables to control as theoretically the load by the body weight to the fractured part of the leg, it may be expected that the usefulness thereby will become greater. In this sense, the necessity to improve the load removing effect of the cast has been highlighted as a focus of attention.

Prior art lower leg casts are also known where the cast portion surrounding the lower leg is short and does not reach the area adjacent the knee of a patient and the rear part adjacent the knee. See, U.S. Pat. No. 2,875,752 by Lovich dated Mar. 3, 1959. Such casts cannot result in reducing the loads applied to the lower leg, even if a space were formed between the foot and bottom of the cast during the preparation of the cast, since the leg is not suspended or supported by the cast adjacent the knee. Such casts are not effective to reduce the load on the lower leg and are not as effective as even the prior art PTB casts described above.

SUMMARY OF THE INVENTION

The present invention has been designed to provide casts which excel in the load removing effect.

The reason why a satisfactory load removing effect could not be obtained by means of the existing cast (of the type as shown in FIGS. 9 and 10) is that since the bearing of the body weight by the cast is insufficient, the load moves, when burdened, in the burdening direction of the leg within the cast, and the foot is pushed up on its sole by the bottom of the cast. The inventor and associates made by test various embodiments of casts for a purpose of improving the load removing effect of the cast for the tibial fracture, and made appreciations and studies on the load removing effect by the dynamic foot pressure analysis system. When a test was prepared for a cast such that a predetermined space is disposed between the sole of the foot and the bottom of the cast, the foot was, during walking, moved or played along the length of a shin bone (in the loading direction of the body weight) in the cast, whereby the push-up by the bottom of the cast toward the sole of the foot could be prevented, and it was found that the load removing effect was largely improved. For easily and exactly comprehending the principle of improving the load removing effect of the PTB cast, the below-mentioned example should be considered.

Imagine a morning-glory or trumpet shaped instrument. If a hand is inserted into the instrument at a flared mouth thereof, the arm is held by a conical interior of the instrument and can no further move ahead. Herein, the trumpet shaped instrument corresponds to the cast and the arm corresponds to the affected leg. A force making the hand go farther corresponds to a load by the body weight. Namely, with respect to the conventional cast for fractured leg, the prior art intended that the leg was supported in the interior cavity of the cast which was presumed as the hollow conical column. However, since the cast and the leg are very imperfect figures as conical bodies, a dynamic bearing power is limited in itself, and the leg somewhat slides within the cast due to the body weight toward the sole of the foot. This sliding of the leg causes a push-up to, or reactive force upon, the sole of the foot by the cast, and the push-up hampers the load removing effect. Therefore, by forming a space between the sole of the foot and the bottom of the cast, the factor of hampering the load removing effect can be taken away even if the leg slides within the cast. Thus, a satisfactory load removing effect can be made available.

Stated another way, the load removing lower leg cast of the prior art supports, at an upper portion of the lower leg part of the cast surrounding the entire part of the patient's lower leg, only a portion of the reactive forces caused by the patient's walking, and all of the remaining part of the loading forces are received at the interior bottom of the cast, bearing against the sole of a patient's foot, so that a satisfactory load removing effect could not be provided. In accordance with the present invention, however, the reactive loading force at the interior bottom of the cast is removed by the space between the sole of the foot and the bottom of the cast, and is also received at the upper portion of the lower leg cast in accordance with the morning-glory or trumpet theory mentioned above, thereby obtaining the effect of canceling the absolute total amount of the reactive loading forces acting upon the foot and the tibial fractured part, that is, a sufficient load removing effect is achieved. Further, when the size of the space is changed, the load removing effect may also be controlled.

Thus, the present invention has been devised on the basis of a new finding, wherein a casting plaster is surrounded around the patient's leg such that a predetermined space is formed between the sole of the foot and the bottom of the cast. The cast prepared by the invention has excellent load removing and walking effect.

As the embodiments of the invention, there will be identified an embodiment fixed as it is attached to the sole of the foot (FIGS. 2, 6 and 7), and another embodiment held as it is attached to a heel, a portion of this embodiment being extended downward further than the heel (FIG. 8).

Further, when an elastic material is disposed in the space and is attached or placed adjacent to the sole of the foot, the thickness of the space after having been secured is varied when walking between the sole of the foot and the bottom of the cast, so that removing effect may be controlled thereby.

For members to be arranged for the space, it is possible to, if applicable to the sole of the foot, employ various kinds of existing members including plate shapes (10 to 30 mm thickness), box shapes, and if incorporating absorption function when shocking of the load, bellows bags, sponge or spring as illustrated and stated later are preferable.

The cast is formed with a predetermined space therebetween. If the patient walks with the leg cast, the foot can be moved or played in the space along the length of the shin bone (in the loading direction) within a predetermined range. This play absorbs an impact force or the load reactive force which would otherwise adversely influence the fractured bone of the leg, and thus a satisfactory load removing effect is made available.

BRIEF DESCRIPTION OF THE DRAWINGS

FIGS. 1(a)–(c) show a first embodiment, in which FIG. 1(a) is a front view of this embodiment, FIG. 1(b) is a plan view of the same, and FIG. 1(c) is a side view thereof.

FIGS. 2(a)–(c) show the condition of the cast provided by the first embodiment in use, in which FIG. 2(a) is a front view of this condition, FIG. 2(b) is a plan view of the same, and FIG. 2(c) is a side view thereof.

FIGS. 3(a)–(c) show the bellows bag, in which FIG. 3(a) is a front view of this embodiment, FIG. 3(b) is a plan of the same, and FIG. 3 (c) is a side view thereof.

FIGS. 4(a)–(b) show expansion and contraction of the bellows bag, in which FIG. 4(a) is a case of the former, and FIG. 4(b) is a case of the latter.

FIGS. 5(a)–(d) show a second embodiment in which FIG. 5(a) is a cross sectional front view of this embodiment, FIG. 5(b) is a plan view of the same, FIG. 5(c) is a side view thereof, and FIG. 5(d) is a side view thereof.

FIGS. 6(a)–(c) show the second embodiment in which FIG. 6(a) is a cross sectional front view of this embodiment, FIG. 6(b) is a plan view of the same, and FIG. 6(c) is a side view thereof.

FIGS. 7(a)–(b) show a third embodiment in which FIG. 7(a) is a cross sectional front view illustrating an expansion of the spring, and FIG. 7(b) is a view illustrating a contraction of the same.

FIGS. 8(a)–(c) show a fourth embodiment in which FIG. 8(a) is a perspective view of this embodiment, FIG. 8(b) is a side view of the same, and FIG. 8(c) is a view showing the use thereof.

FIGS. 11(a)–(e) show a fifth embodiment in which FIG. 11(a) is a side view of this embodiment, FIG. 11(b) is a side view of the same, FIG. 11(c) is a side view of the same, FIG. 11(d) is a side view thereof, and FIG. 11(e) is a side view thereof.

FIGS. 12(a)–(b) show a sixth embodiment in which FIG. 12(a) is a side view of this embodiment, and FIG. 12(b) is a plan view of the same.

FIGS. 13(a)–(c) show a seventh embodiment in which FIG. 13(a) is a side view of this embodiment, FIG. 13(b) is a plan view of the same and FIG. 13(c) is a front view thereof.

PREFERRED EMBODIMENTS OF THE INVENTION

Figure 8A:
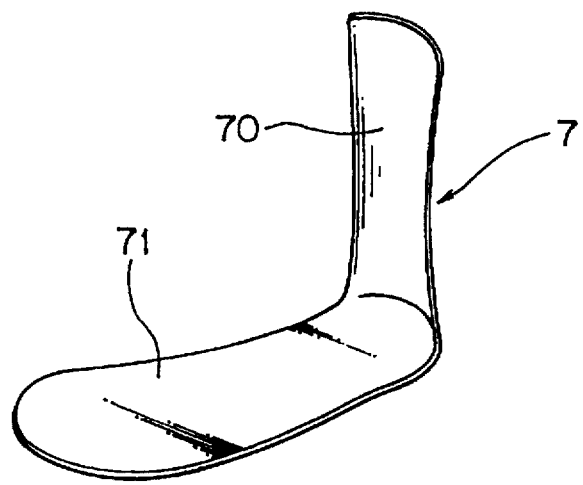
Figure 8B:
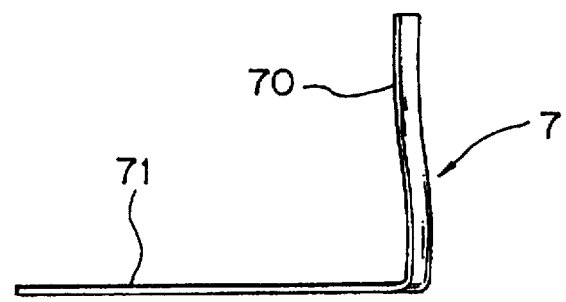

Reference will be made to the steps of making the cast by means of the instruments exemplified herein. FIG. 8 shows a most basic embodiment of this invention, from which other embodiments are derived. However for easy understanding of the invention, explanation will be made with FIG. 8 as a fourth embodiment.

Figure 1A:
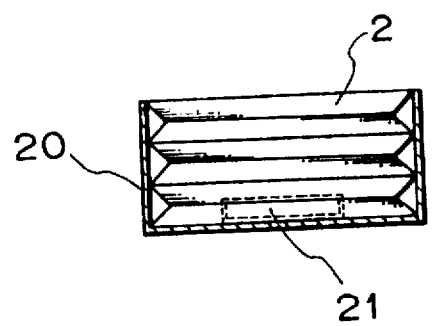
Figure 1B:
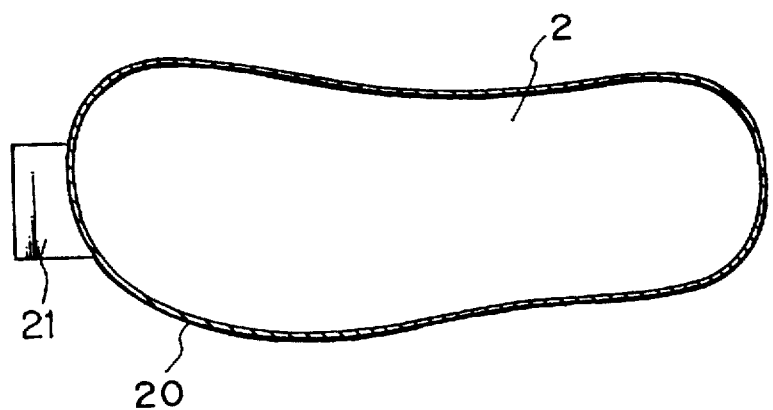
Figure 1C:
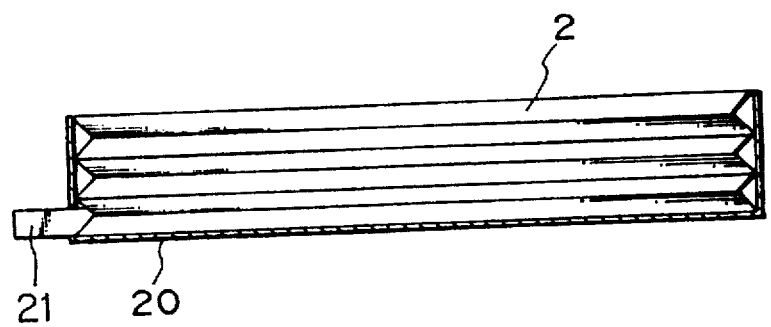
Figure 3A:
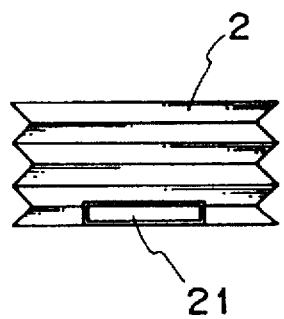
Figure 3B:
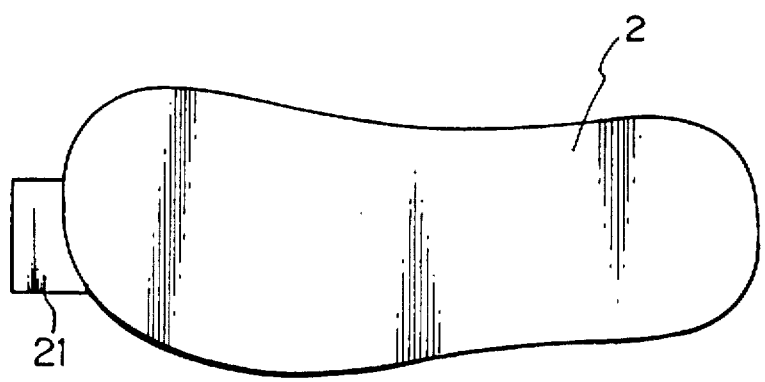
Figure 3C:
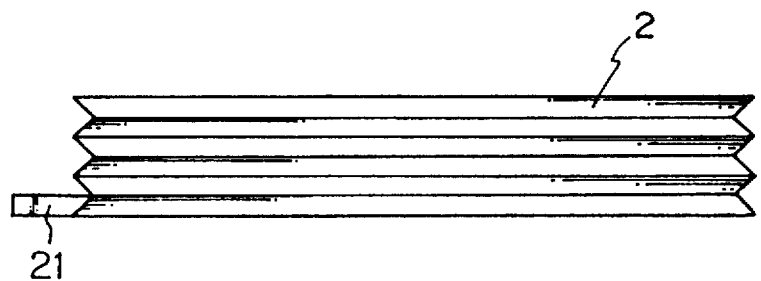
Figure 4A:
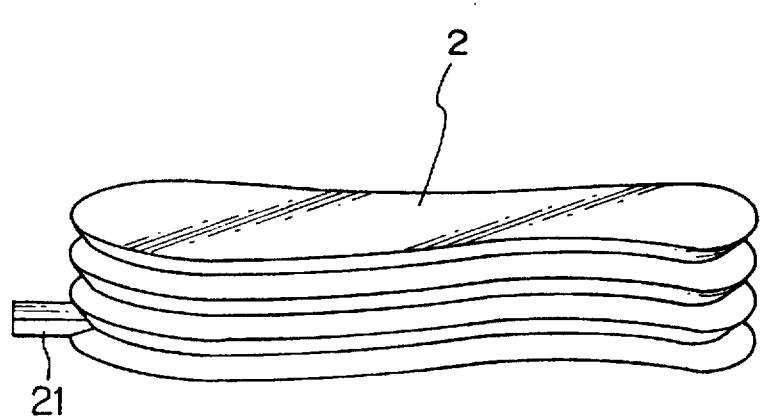
Figure 4A:
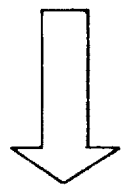
Figure 4B:
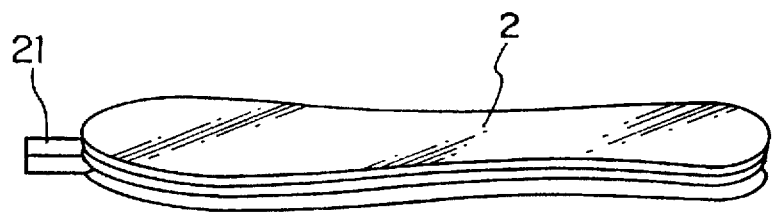
Figure 5A:
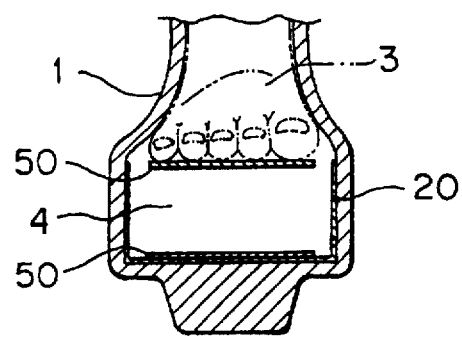
Figure 5B:
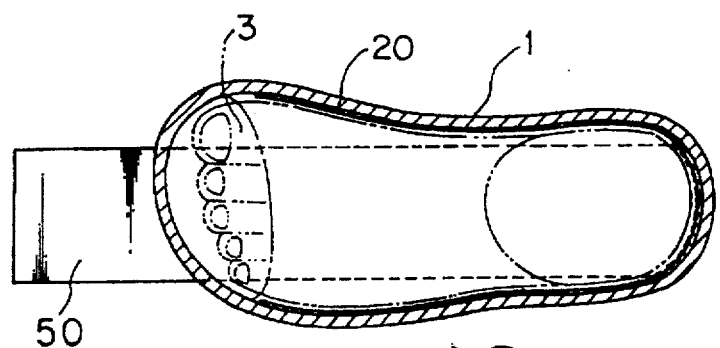
Figure 5C:
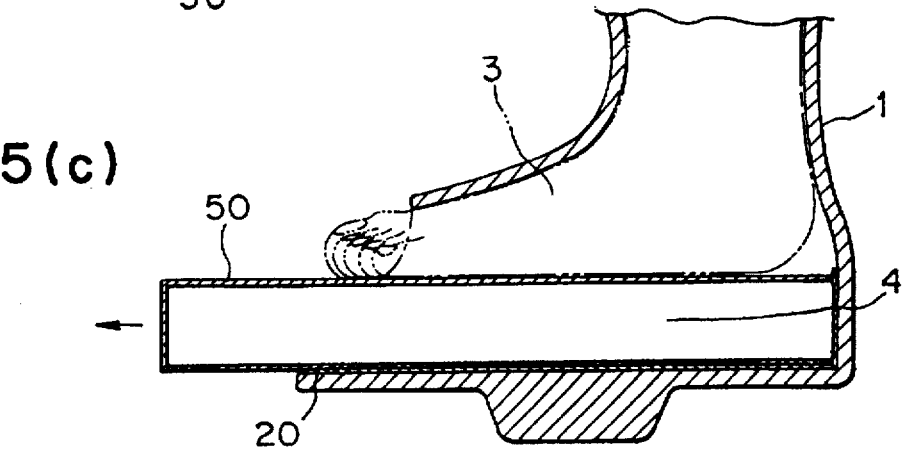
Figure 5D:
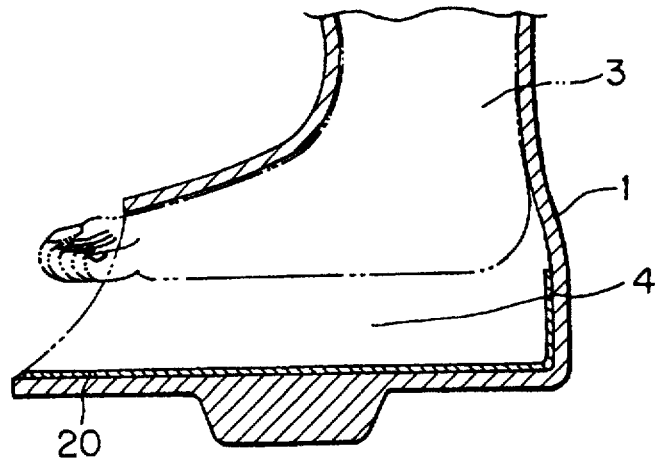

The bellows bag 2 is closed at an air hole 21 as seen in FIG. 3 and is disposed within a protecting case 20 comprising a hard resin as illustrated in FIG. 1. A foot 3 is then put on the bellows bag 2, followed by wrapping the casting plaster on the foot in an ordinary sequence and hardening it. When wrapping and hardening the casting plaster, a considerable pressure is burdened on the bellows bag 2, however it may perfectly maintain its shape against the pressuring force, since it is placed within the hard protecting case 20 and the air hole 21 is tightened or closed. When the air hole 21 is opened after the plaster 1 is solidified, the bellows bag 2 is made to freely expand and contract as is seen in FIG. 4, and the load removing and walking cast having excellent load removing effect is accomplished.

The protecting case 20 serves to protect the soft and elastic bellows bag 2 against the cast 1 wrapped around the patient's leg, and due to this protecting service, the bellows bag 2 may expand and contract vertically (along the length of the shin bone) even by a weak pressure within the cast 1.

Figure 2A:
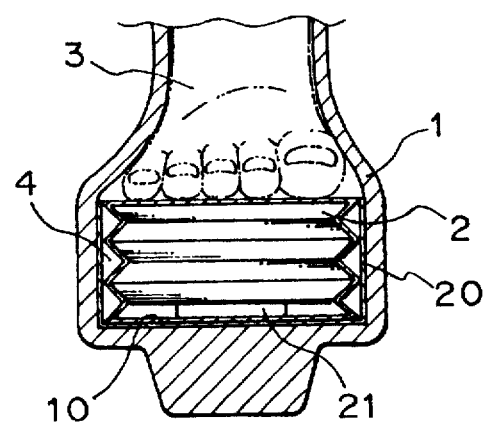
Figure 2B:
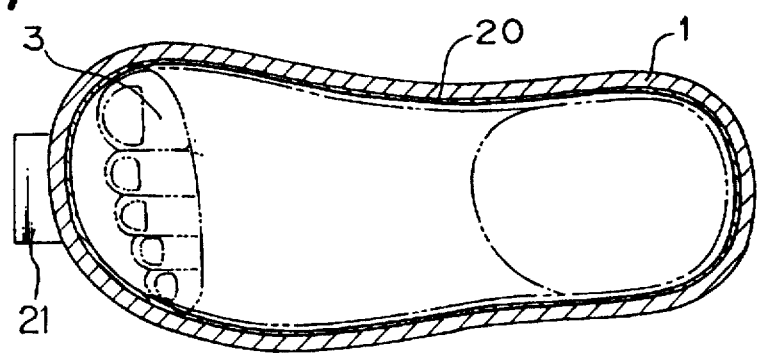
Figure 2C:
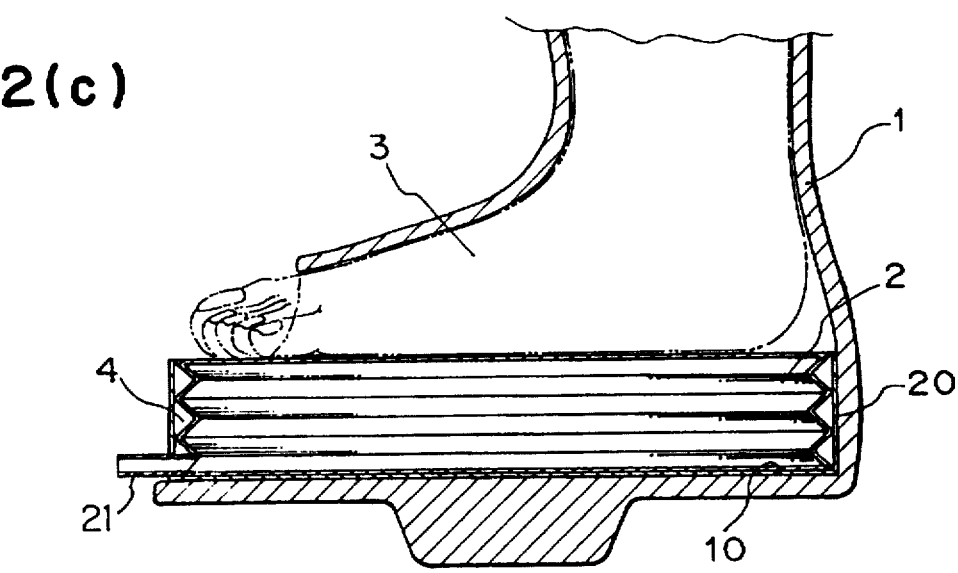

As shown in FIG. 2, the space 4 exists between the sole of the foot 3 and the bottom 10 of the cast 1, and the protecting case 20 made of the hard synthetic resin is disposed in the space 4, within which the bellows bag 2 is placed. The bellows bag 2 communicates with the exterior through the air hole 21, and expands and contracts in response to moving of the foot as the patient walks as burdened. Therefore, when walking with the present cast 1, the bellows bag 2 placed in the space 4 is pressured and easily shrinked, and the foot 3 may moderately or slightly move along the length of the shin bone (in the loading direction) within the space 4, and this moving partially absorbs the loading force by the walking burden. Thus, as will be later exemplified, a sufficient load removing effect may be provided.

The load removing and walking cast 1 of the embodiment described above, and indeed of each of the embodiments of the invention described herein, extends downward from the knee region, and is shaped at the knee region in a manner that catches around the knee and its adjacent parts. The leg of a patient is thus suspended by the shape of the cast with respect to the leg together with the pressure of the cast with respect to the leg adjacent the front and rear parts of the knee. That is, due to the shape of the cast and the catching or holding of the lower leg at the knee and the rear part of the knee by the cast, the leg is suspended and does not slide down, or slides down only slightly less than the distance of the space that is formed between the sole of the foot and the interior bottom portion of the cast. The suspension of the lower leg at the knee region in accordance with the teachings of the inventive cast as described, along with the maintaining of a sufficient space between the sole of a foot and the interior portion of the cast, is an important feature of the present invention to remove or substantially lessen the reactive forces caused by walking upon the lower leg.

Preparing process using the instrument employed in the instant embodiment will be explained in that a space holding instrument 50 of U shape in cross section is inserted at an opened end of the protecting case 20, the foot 3 lying on the upper plate of the instrument, and a casting plaster is surrounded thereon in an ordinary manner and is hardened. After the plaster has been solidified, the instrument 50 is pulled out so that a space 4 requisite for removing the load is formed between the sole of the foot 3 and the interior bottom portion of the cast.

Figure 6A:
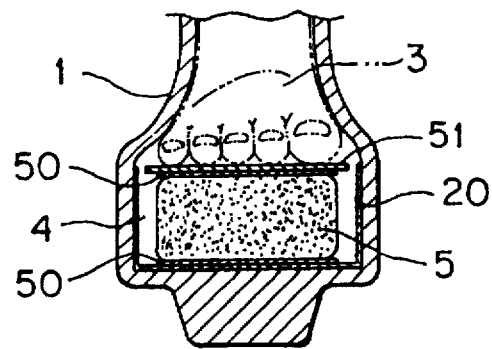
Figure 6B:
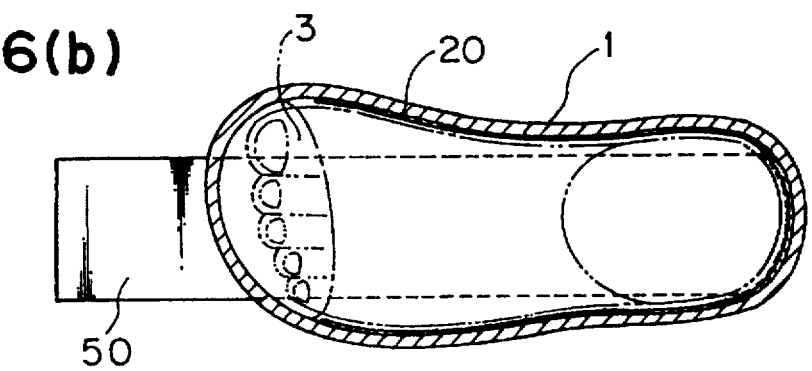
Figure 6C:
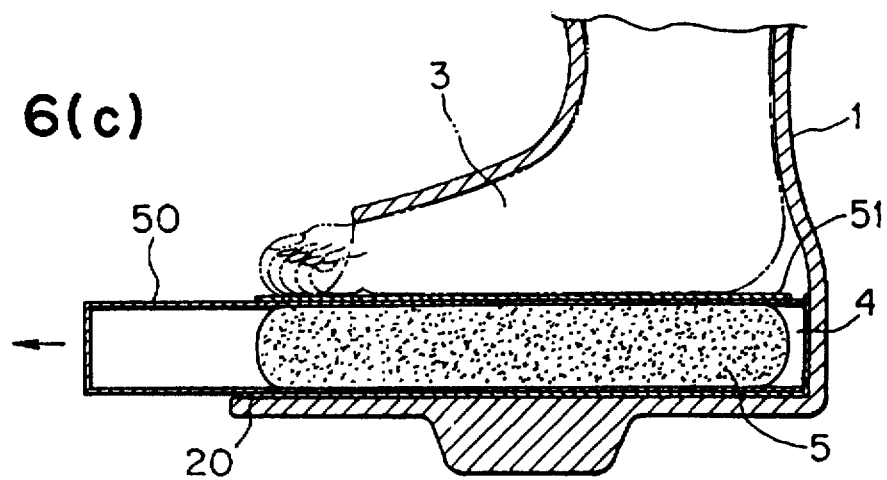
Figure 7A:
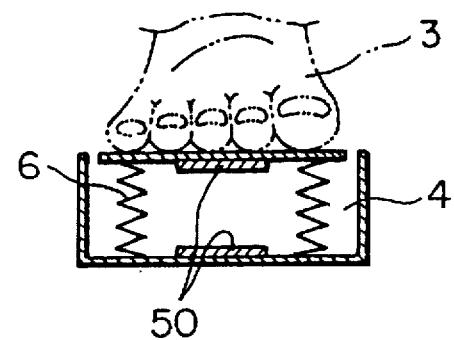
Figure 7B:
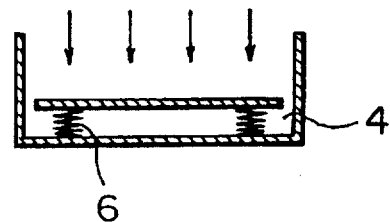

FIGS. 5 and 6 illustrate a second embodiment, and FIG. 7 shows a third embodiment, and these embodiments employ the sponge and the spring respectively, in place of the bellows bag 2 of the first embodiment.

A further explanation will be made to the process of preparing or making the cast of the second embodiment. A space holding or maintaining instrument 50 is inserted into a front opening part of the protecting case 20, said space holding instrument being of a rectangle opening one of vertical sides in cross section (]) and holding a sponge 5 with its upper and lower sides. A bottom plate 51 is placed on an upper plate of the space holding instrument 50, and the foot 3 is put on the bottom plate 51, followed by wrapping the casting plaster around the patient's foot by the ordinary means.

The space holding instrument 50 is removed after the plaster has been solidified. Then, the space 4 appears between the sole of the foot 3 and the bottom of the cast 1, and the sponge 5 elastically acts within the space 4. Thus, the cast is completed. The process of the third embodiment is similar to the second embodiment, in which depending upon the space holding instrument 50, the space 4 appears, similarly therebetween, and a spring 5 expands and contracts within the space 4.

Also in the use of the cast 1 produced by these embodiments, when walking, the foot 3 may moderately move or slide slightly within the cast along the length of the shin bone (in the loading direction), so that the loading force caused by the walking burden is fully absorbed.

Figure 8C:
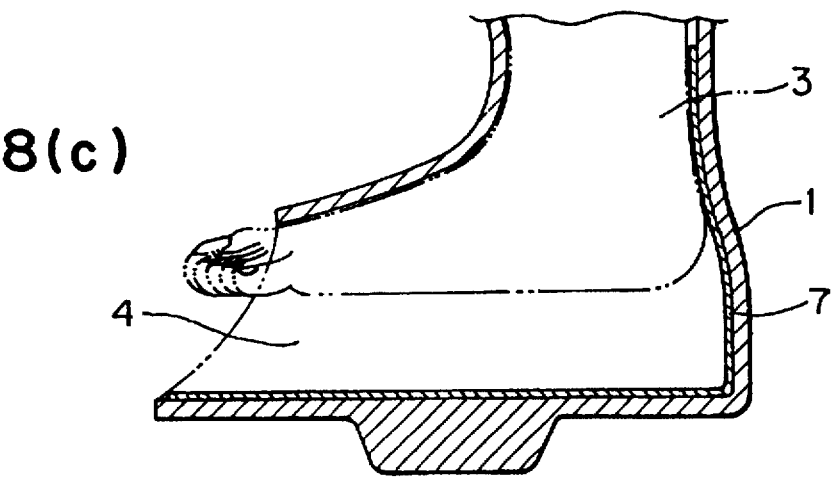

FIG. 8 illustrates a fourth embodiment. As shown in FIG. 8(c), a space is formed between the sole of a patient's foot and the interior bottom base portion of the cast. A similar space is also formed in the first to third embodiments, in which, however, the elastic member is interposed in the space so as to control the load removing and walking effect.

The substantially L-shaped member 7 is used to form the space between the sole of the foot 3 and the bottom of the cast 1 during the preparation of the cast. The member or protecting plate 7 of this embodiment is L-shaped in cross section or a bent plate member comprising a side 70 contacting a heel of the foot, and slightly above near the calf, and a bottom 71 forming a substantially planar base and contacting the bottom of the cast 1 after the cast is solidified.

The process for preparing the cast of this embodiment brings the heel to the side 70 such that a space is formed between the sole of the foot 3 and the bottom 71 of the protecting plate, and it is sufficient to wrap and solidify the casting plaster under a condition that the lower portion of the side 70 extends further downward than the heel so as to form the space 4.

In this embodiment, a cast like a morning-glory or trumpet is formed leaving the space between the sole of the foot and the bottom of the protecting plate 7 as seen in FIG. 8(c). The sole of the foot does not contact the bottom 71 due to suspending the lower leg by holding the lower leg at the knee and its adjacent parts, so that the space 4 is maintained during walking. The reactive forces caused by walking are taken up through the cast and are at least partially borne at the upper portions of the lower leg adjacent the knee (front and rear), as previously described.

The embodiment of FIG. 8 does not employ any intermediates such as the bellows, the spring or the sponge between the sole of the foot and the bottom of the cast, however the cast of this embodiment can also make a space for avoiding the push-up, and bring about the satisfied load removing and walking effect by moving of the foot within the space while walking.

Figure 9:
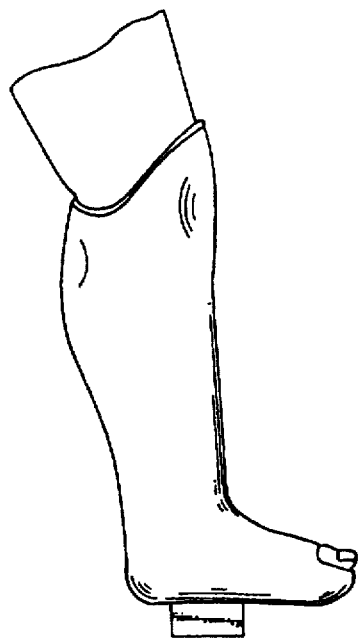
FIG. 9 is an explanatory view showing a conventional leg cast (PTB cast).
Figure 10:
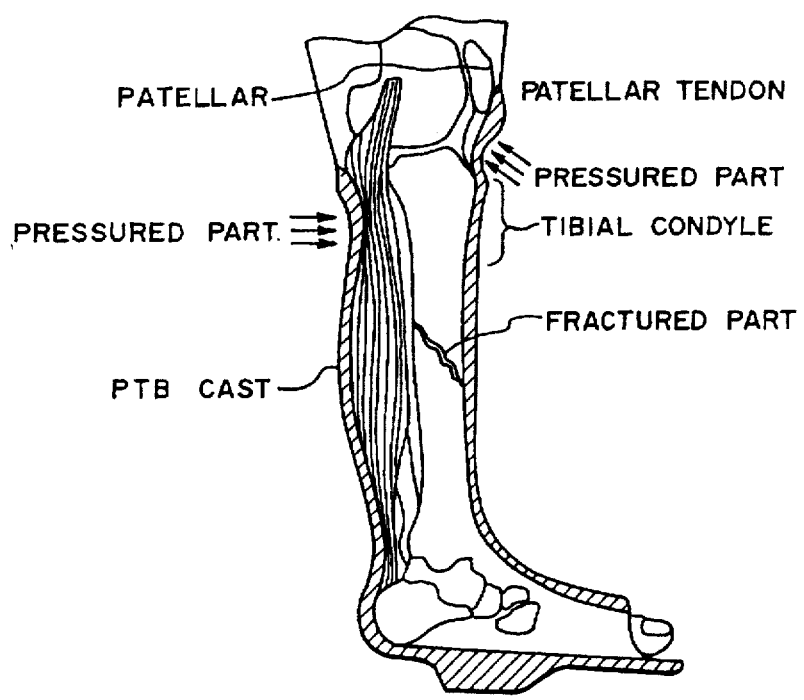
FIG. 10 shows parts aiming at supporting of a patient's human body weight (pressuring parts) in the above conventional leg cast (PTB cast), the supporting and pressurized portion of the cast also used in the above embodiments of the present invention.
Figure 11A:
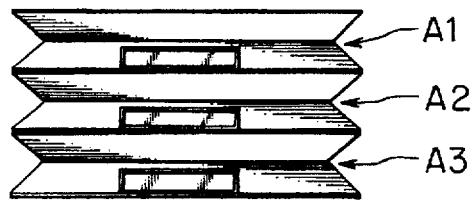
Figure 11B:
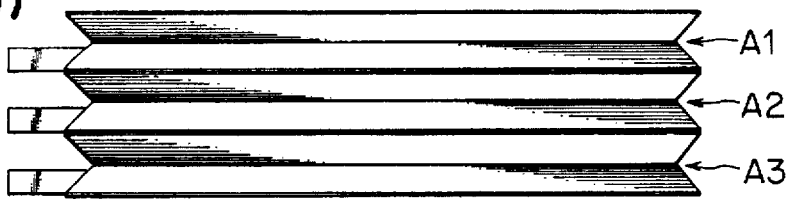
Figure 11C:
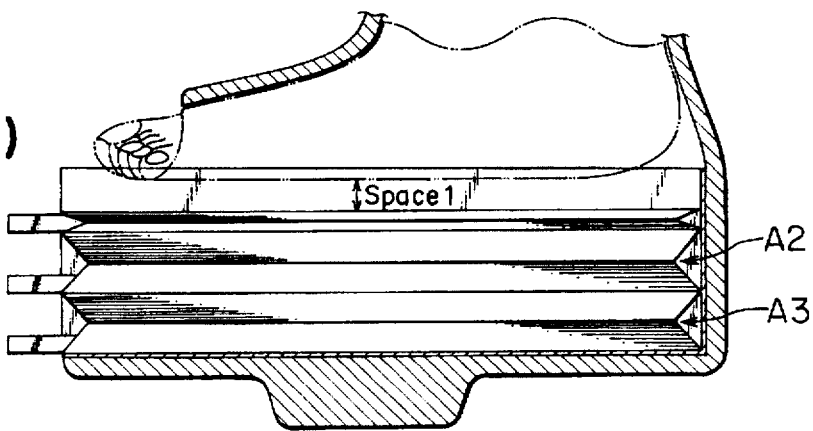
Figure 11D:
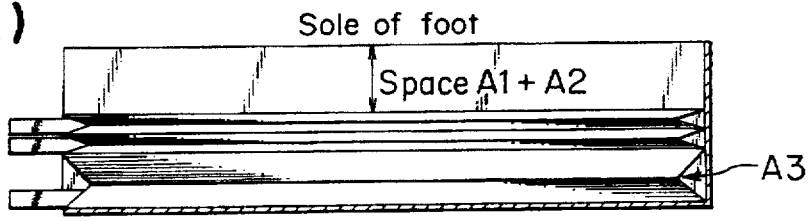
Figure 11E:
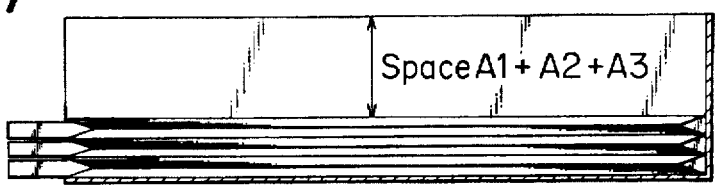

With respect to the above embodiments, the load removing and walking effects were tested using the dynamic foot pressure analysis system comparing with the prior art as shown in FIGS. 9 and 10.

The prior PTB cast of FIGS. 9 and 10 showed that the load removing effect was only 30.5% of the human body weight, while the load removing and walking effect of the present invention when the cast having the space distance of 1 cm (10 mm) was 55.9%, that in a case of 1.5 cm (15 mm) was 65.8%, that of 2.5 cm (25 mm) was 93.7%, and that of 3 cm (30 mm) was 100% which was the perfect load removing and walking effect.

As explained at length, the leg casts provided by means of the invention bring about remarkable results to largely improve the load removing and walking effect.

It should be appreciated that the cast of the present invention can extend above the knee and may extend to the hip. Such a cast may support the hip bone and provide load removal upon the entire leg including load removal at the thigh.

It may be appreciated that the embodiments using the elastic member provide for controlling the load removing effect. The elastic member which may vary the space, controls the load removing effect. That is, for healing the tibial fracture, a sufficient load removing effect is required immediately after suffering the tibial fracture. It is said that a callous appears around the fractured part as time goes on, and a moderate burden upon the fractured part advantageously acts on the bone formation. However, the prior art cast did not bring about a sufficient load removing effect required at the beginning period of curing the fractured bone, and, further, it was impossible to control the load removing effect in accordance with the curing progress. In contrast, in the present invention, as above exemplified, the load removing effect can be varied by changing the thickness of the elastic member. Therefore, if using the elastic members of different thicknesses in response to the curing progress, the load removing effect may be controlled, and it may be served as an optimum curing instrument.

The present invention proposes bellows bags as illustrated in FIGS. 11 to 14 as further embodiments for controlling load removing effects. These new embodiments have been further improved of the bellows bags shown in FIGS. 1 to 4.

References will be made to FIGS. 11 to 14. Basic principles or disposals thereof within the cast are not different from those of the aforementioned bellows members, in which, however, the working function is more enhanced so that basically the foregoing bellows are divided into or are made two independent bellows parallel. Depending upon means of making the divided or parallelled embodiments, uses other than the above cases may be available as will be referred to below.

A first using embodiment is that the bellows is divided into a plurality of upper and lower independent spaces by means of interior isolating walls.

FIG. 11 shows that the bellows is divided into independent three spaces A1, A2, A3 by the interior partitioning walls, and each of the spaces is equipped with a one air hole, whereby the bellows can be shrinked (shortened in width) by selectively operating the air hole, that is, the spaces for the foot's sliding are enlarged three stepwise. If the air hole is provided with a re-sealing stopper, an arbitrary space which has once been opened at the air hole and shrinked, is again expanded by introducing the air, so that the width of the space may be reduced.

In FIG. 11, (a) and (b) show the bellows prior to opening the air hole, where the spaces A1, A2 and A3 are elongated due to the pressure of the enclosed air. (c) shows that the air hole of the space A1 is opened and only the space A1 is shrinked (shortened) to provide a space 1. Similarly, (d) shows that the air holes of the spaces A1, A2 are opened, and (e) shows that the air holes of the spaces A1, A2, A3 are opened, and the space A1+A2 and the space A1+A2+A3 are obtained, respectively.

If the air hole is provided with the re-sealing stopper, it is possible to return the shrinked bellows to an elongated state as a sequence of (e)→(d)→(c)→(b), and as a result such a load removing effect may be optionally provided alongside a curing progress while maintaining the bellows within the cast which does not require re-making.

Figure 12A:
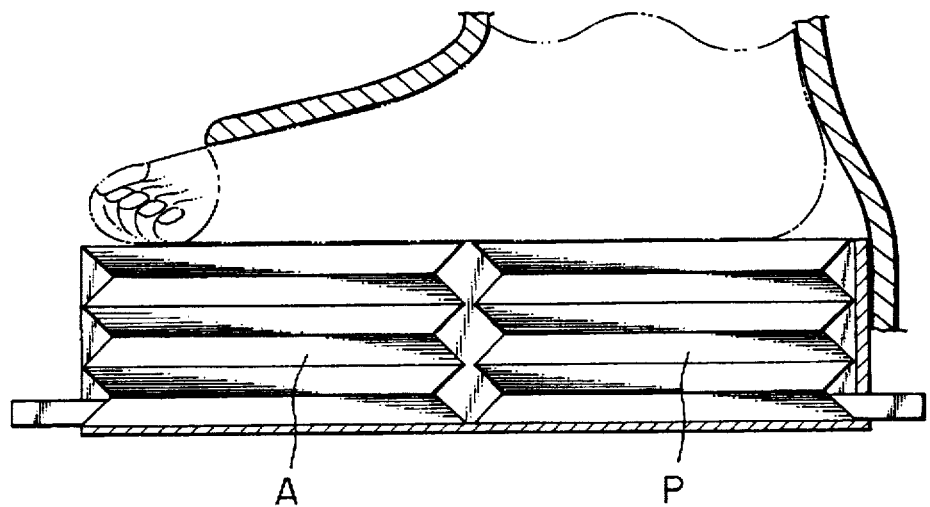
Figure 12B:
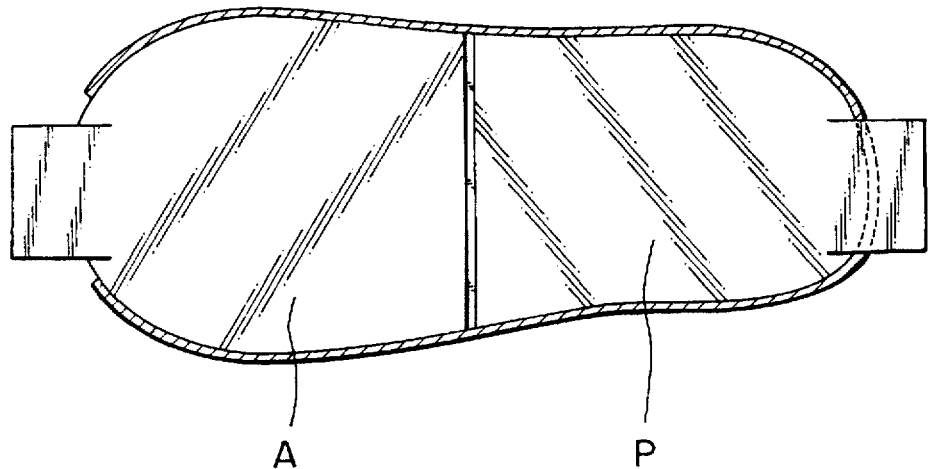

A second embodiment illustrated in FIG. 12 are the bellows divided into two parts A and P of back and forth. Thus, side walls of the two bellows face one another therebetween, differently from the first embodiment. Since two bellows have individual air holes, each of them may be shortened or elongated independently.

The instant embodiment may be clinically used to bone fractures at front parts of foot or heel (rear part of foot). That is, if the bellows A of the front part is shortened, a load is burdened on the not shortened bellows P of the heel part, and thus the load is removed from the foot front part, and reversely if the rear bellows (the space) is shortened, the load is effected on the front part and the heel is removed from the load.

Figure 13A:
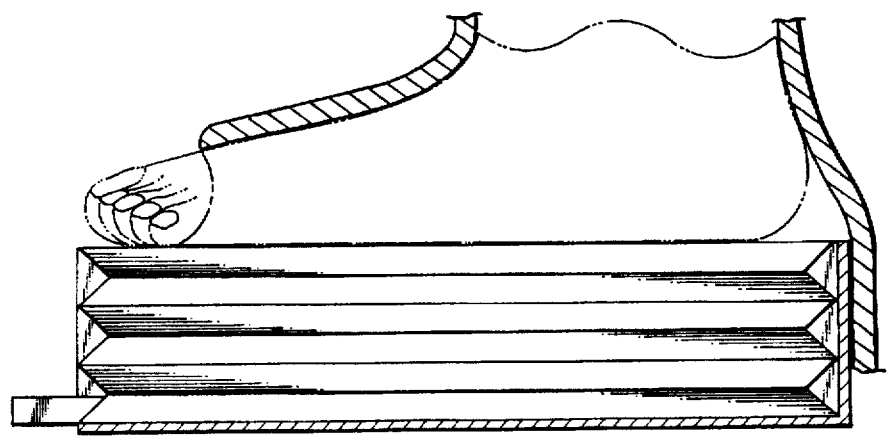
Figure 13B:
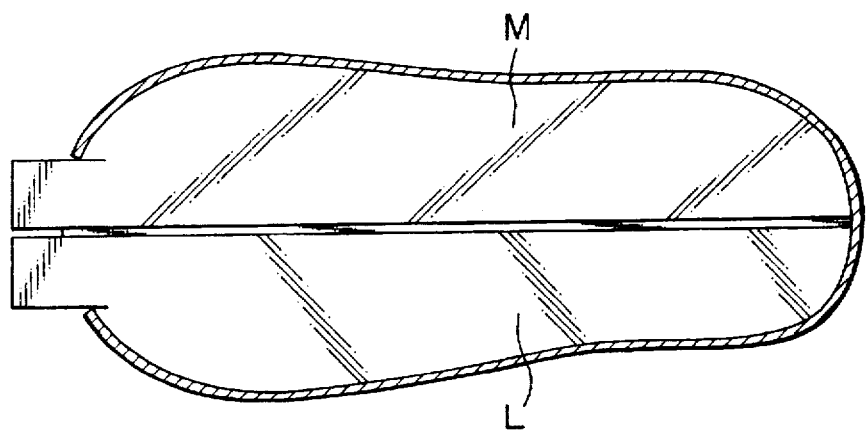
Figure 13C:
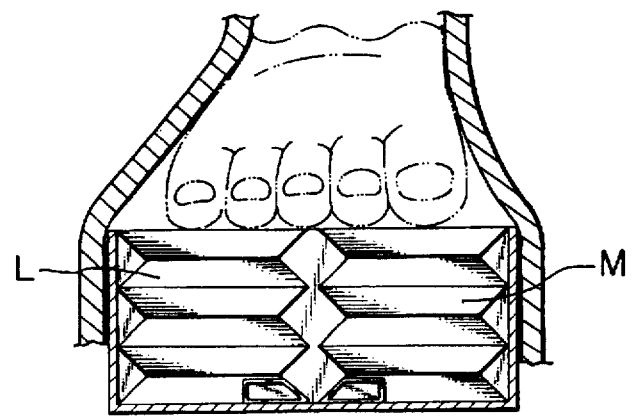

FIG. 13 shows a third embodiment that the bellows is divided at center longitudinally into independent right M and left L. The two bellows have independent air holes, and each of them may be shortened or elongated independently as the second embodiment does.

This embodiment is used when the inner part of the foot (i.e. a great toe) or the outer part (i.e. a little toe) is selectively effected with load removal. Using ways are similar to those of the second embodiment in that a part to be removed from load is shortened (shrinked).

Figure 14:
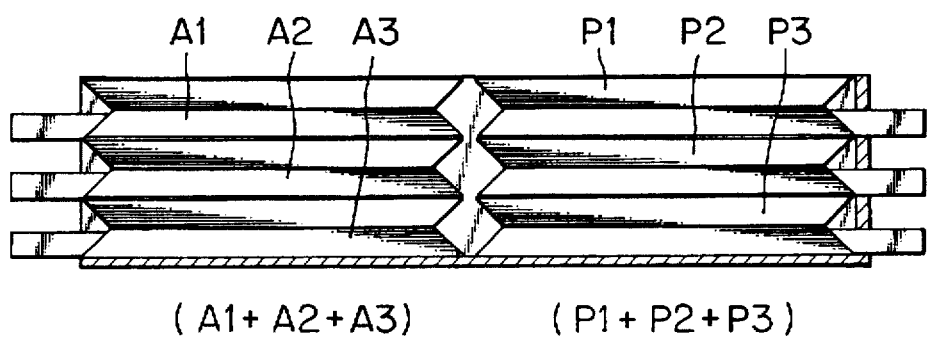
FIG. 14(a) is a reference view.

FIG. 14 shows a fourth embodiment which is combined with the second embodiment or the first+third embodiments. Although a structure is complicated, the load may be removed per each of the independent bellows.

I claim:

1. A load removing and walking cast for surrounding the lower leg and foot of a patient and supporting a load comprising, a leg surrounding plaster cast portion for surrounding the lower leg and foot of a patient and supporting a load and a plaster cast bottom portion including an interior bottom base portion, and load removing means for reducing the loading forces upon a patient's lower leg and foot during the imposition of reactive loading forces upon the cast, said load removing means disposed within a space between the interior base portion and the sole of a patient's foot and including an elastic member comprising a bellows bag formed of soft resin lying upon said interior base portion and extending within the space between the interior base portion and the sole of a patient's foot said bellows bag being divided into at least upper and lower independent superimposed spaces separated by a partition, each of said superimposed spaces provided with an air stopper at an air hole.

2. A load removing and walking cast for surrounding the lower leg and foot of a patient and supporting a load comprising, a leg surrounding plaster cast portion for surrounding the lower leg and foot of a patient and supporting a load and a plaster cast bottom portion including an interior bottom base portion, a rigid protective casing having a substantially planar casing base and casing sidewalls extending from the casing base, said protective casing lying upon said interior bottom base portion, and load removing means for reducing the loading forces upon the sole of a patient's lower leg during the imposition of reactive loading forces on the cast, said load removing means disposed within a space between said substantially planar casing base and the sole of a patient's foot and including an elastic member disposed within said protective casing and lying upon the said casing base, said elastic member comprising a bellows bag formed of soft resin and including an air hole for enabling air to pass into and out of said bellows bag, and said protective casing including an opening adjacent said bellows bag air hole to enable the air passage, said bellows bag being divided into at least upper and lower independent superimposed spaces separated by a partition, each of said superimposed spaces provided with an air stopper at an air hole.

3. The cast of claim 1 wherein an interior space is divided into three independent parts by means of partitioning walls, and each of the divided spaces is provided with an air stopper at an air hole.

4. A load removing and walking cast for surrounding the lower leg and foot of a patient and supporting a load comprising, a leg surrounding plaster cast portion for surrounding the lower leg and foot of a patient and supporting a load and a plaster cast bottom portion including an interior bottom base portion, and load removing means for reducing the loading forces upon the sole of a patient's lower leg during the imposition of reactive loading forces upon the cast, said load removing means disposed within a space between the interior base portion and the sole of a patient's foot and including an elastic member comprising a bellows bag formed of soft resin lying upon said interior base portion and extending within the space between the interior base portion and the sole of a patient's foot, wherein the bellows bag is laterally divided into two parts at its center.

5. A load removing and walking cast for surrounding the lower leg and foot of a patient and supporting a load comprising, a leg surrounding plaster cast portion for surrounding the lower leg and foot of a patient and supporting a load and a plaster cast bottom portion including an interior bottom base portion, and load removing means for reducing the loading forces upon the sole of a patient's lower leg during the imposition of reactive loading forces upon the cast, said load removing means disposed within a space between the interior base portion and the sole of a patient's foot and including an elastic member comprising a bellows bag formed of soft resin lying upon said interior base portion and extending within the space between the interior base portion and the sole of a patient's foot, wherein the bellows bag is longitudinally divided into two parts along its length.

6. A load removing and walking cast for surrounding the lower leg and foot of a patient and supporting a load comprising, a leg surrounding plaster cast portion for surrounding the lower leg and foot of a patient and supporting a load and a plaster cast bottom portion including an interior bottom base portion, a rigid protective casing having a substantially planar casing base and casing sidewalls extending from the casing base, said protective casing lying upon said interior bottom base portion, and load removing means for reducing the loading forces upon the sole of a patient's lower leg during the imposition of reactive loading forces on the cast, said load removing means disposed within a space between said substantially planar casing base and the sole of a patient's foot and including an elastic member disposed within said protective casing and lying upon the said casing base, said elastic member comprising a bellows bag formed of soft resin and including an air hole for enabling air to pass into and out of said bellows bag, and said protective casing including an opening adjacent said bellows bag air hole to enable the air passage, said bellows bag being laterally divided into two parts at its center.

7. A load removing and walking cast for surrounding the lower leg and foot of a patient and supporting a load comprising, a leg surrounding plaster cast portion for surrounding the lower leg and foot of a patient and supporting a load and a plaster cast bottom portion including an interior bottom base portion, a rigid protective casing having a substantially planar casing base and casing sidewalls extending from the casing base, said protective casing lying upon said interior bottom base portion, and load removing means for reducing the loading forces upon the sole of a patient's lower leg during the imposition of reactive loading forces on the cast, said load removing means disposed within a space between said substantially planar casing base and the sole of a patient's foot and including an elastic member disposed within said protective casing and lying upon the said casing base, said elastic member comprising a bellows bag formed of soft resin and including an air hole for enabling air to pass into and out of said bellows bag, and said protective casing including an opening adjacent said bellows bar air hole to enable the air passage, said bellows bag being longitudinally divided into two parts along its length.

* * * * *